(12) United States Patent  
Winward et al.

(10) Patent No.: US 9,300,356 B2
(45) Date of Patent: Mar. 29, 2016

(54) MEDICAL CABLE INCLUDING AUTHENTICATION CIRCUIT

(71) Applicant: ICU Medical, Inc., San Clemente, CA (US)

(72) Inventors: Kelsey Brendon Winward, San Clemente, CA (US); Kwok-Kwong Wong, Sunnyvale, CA (US); Douglas B. MacDonald, Los Gatos, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 14/514,299

(22) Filed: Oct. 14, 2014

(65) Prior Publication Data

US 2015/0155912 A1 Jun. 4, 2015

Related U.S. Application Data

(63) Continuation of application No. PCT/US2013/032609, filed on Mar. 15, 2013.

(60) Provisional application No. 61/624,970, filed on Apr. 16, 2012.

(51) Int. Cl.
- *H04B 3/46* (2015.01)
- *H04B 3/02* (2006.01)
- *A61B 5/0215* (2006.01)
- *A61B 5/01* (2006.01)

(Continued)

(52) U.S. Cl.
CPC *H04B 3/02* (2013.01); *A61B 5/015* (2013.01); *A61B 5/0215* (2013.01); *G06F 19/3412* (2013.01); *A61B 2017/00482* (2013.01); *A61B 2562/226* (2013.01)

(58) Field of Classification Search
CPC ...... H04B 3/02; G06F 19/3412; A61B 5/015; A61B 5/0215
USPC .......................................... 375/224, 227, 228
See application file for complete search history.

(56) References Cited

U.S. PATENT DOCUMENTS

| 6,298,255 | B1 | 10/2001 | Cordero et al. |
| 6,307,476 | B1 | 10/2001 | Smith et al. |

(Continued)

FOREIGN PATENT DOCUMENTS

WO    WO 2013/158314    10/2013

OTHER PUBLICATIONS

International Search Report and Written Opinion re PCT Application No. PCT/US2013/032609, mailed Jun. 4, 2013.

(Continued)

*Primary Examiner* — Kevin Kim
(74) *Attorney, Agent, or Firm* — Knobbe Martens Olson & Bear LLP

(57) ABSTRACT

Medical cable authentication apparatuses and methods are disclosed. Some embodiments herein provide a medical cable assembly for use in a patient monitoring system including authentication circuit. The authentication circuit can provide a signal indicative of whether the medical cable assembly is compatible, or desirable for use with a particular patient monitor and/or sensor. The authentication circuit can include a substantially constant current source that drives a capacitor, wherein a voltage signal provided by a patient monitor drives the current source, and the voltage across the capacitor is used to generate an authentication output signal.

34 Claims, 12 Drawing Sheets

(51) Int. Cl.
*G06F 19/00* (2011.01)
*A61B 17/00* (2006.01)

(56) References Cited

U.S. PATENT DOCUMENTS

| 8,764,668 B2 | 7/2014 | Roteliuk et al. |
| 2003/0163052 A1 | 8/2003 | Mott et al. |
| 2006/0161054 A1 | 7/2006 | Reuss et al. |
| 2011/0057881 A1* | 3/2011 | Wen et al. .................. 345/163 |

OTHER PUBLICATIONS

International Preliminary Patent Report re PCT Application No. PCT/US2013/032609, mailed Mar. 17, 2015.

* cited by examiner

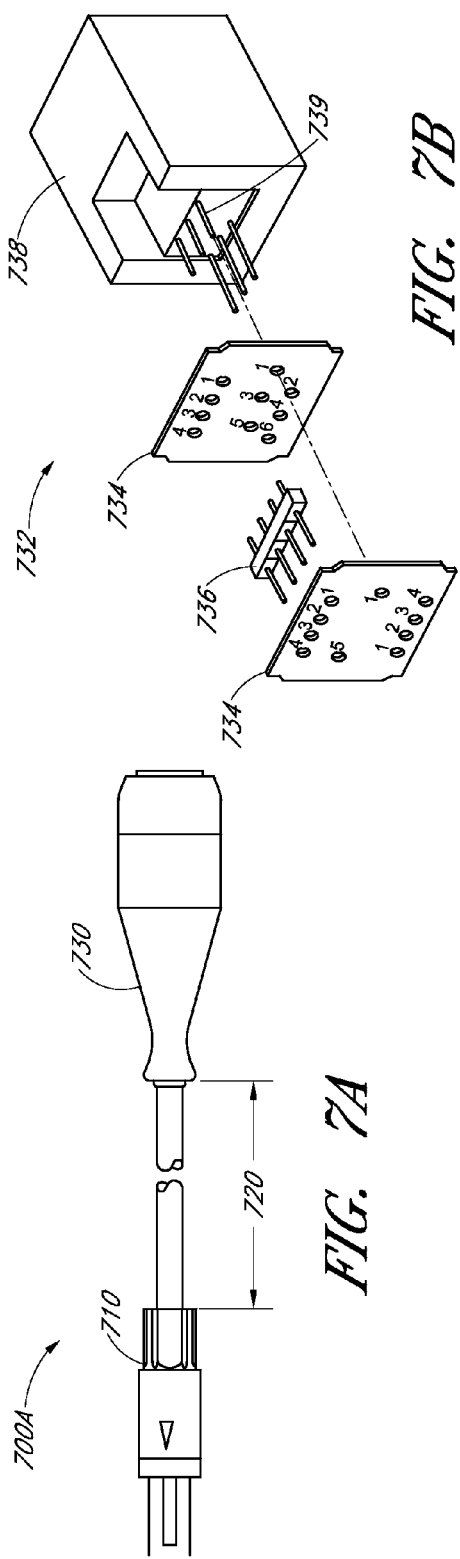
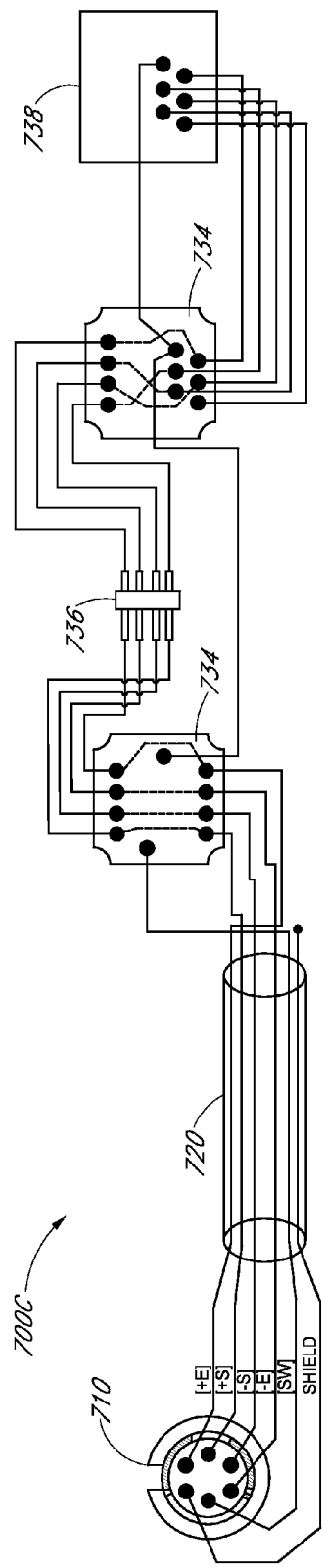
FIG. 7A
FIG. 7B
FIG. 7C

MEDICAL CABLE INCLUDING AUTHENTICATION CIRCUIT

RELATED APPLICATIONS

This application claims the benefit under 35 U.S.C. §120 and U.S.C. §365(c) as a continuation of International Application No. PCT/US2013/032609, designating the United States, with an international filing date of Mar. 15, 2013, titled MEDICAL CABLE INCLUDING AUTHENTICATION CIRCUIT, which claims the benefit of U.S. Provisional Patent Application No. 61/624,970, filed Apr. 16, 2012, titled MEDICAL CABLE INCLUDING AUTHENTICATION CIRCUIT, the entirety of each of which is incorporated by reference herein and made a part of this specification.

BACKGROUND

In certain circumstances, the diagnosis and treatment of certain physiological ailments and conditions may be aided by the use of various medical sensors that are configured to detect one or more physiological parameters of a patient. Medical sensors may be configured to communicate with one or more patient monitors that receive information from a sensor for various purposes. Sensors may be disposable-type sensors in order to reduce the risk of contamination from multiple or prolonged uses of a single sensor, among other considerations. The electrical and/or physical connection between a sensor and a patient monitor may be facilitated by the use of one or more medical cables through which data and/or power may be transmitted.

SUMMARY

For purposes of summarizing the disclosure, certain aspects, advantages and novel features have been described herein. It is to be understood that not necessarily all such advantages can be achieved in accordance with any particular embodiment disclosed herein. Thus, the features disclosed herein can be embodied or carried out in a manner that achieves or optimizes one advantage or group of advantages as taught herein without necessarily achieving other advantages as can be taught or suggested herein.

Certain embodiments provide a medical cable for transmitting data between a patient monitor and a sensor capable of detecting one or more physiological parameters of a patient. The medical cable may include a first connector configured to be coupled to the patient monitor and a second connector configured to be coupled to the sensor and to receive a sensor signal from the sensor that comprises information related to the one or more physiological parameters.

The medical cable may further include authentication circuitry comprising a substantially constant current source coupled to a capacitor, the authentication circuitry being configured to receive a test signal from the patient monitor and generate, using the current source and the capacitor, an output signal responsive to the test signal that reaches a target voltage within an amount of time expected by the patient monitor.

In certain embodiments, the authentication circuitry is further configured to provide the output signal to the patient monitor. Furthermore, in certain embodiments, the second connector contains a portion of an electrically conductive path in series with a switch, the conductive path configured to transmit the test signal from the patient monitor. The second connector may be configured to close the switch in response to being coupled to the sensor. Closing the switch may allow for at least a portion of the test signal to be provided to the authentication circuitry via the portion of the electrically conductive path. The second connector may be configured to open the switch in response to being uncoupled from the sensor.

In certain embodiments, the authentication circuitry further comprises a buffer amplifier connected to the current source and the capacitor. Furthermore, in certain embodiments, the authentication circuitry may further comprises one or more resistors, wherein a rise time of the output signal at least partially depends on a value of the one or more resistors. The authentication circuitry may comprises a diode, wherein the authentication circuitry is configured such that activation of the diode allows for the capacitor to at least partially discharge through the diode. In certain embodiments, the input signal may be a square wave having a predetermined pulse width. The predetermined pulse width may be between about 100 and about 160 µs, such as between 95 and 165 µs. The predetermined pulse width may be at least partially based on a value of the capacitor.

In certain embodiments, the first connector comprises a housing, the authentication circuitry being contained within the housing. Furthermore, in certain embodiments, the second connector may comprise a housing, the authentication circuitry being contained within the housing.

In certain embodiments, the second connector comprises a plurality circuit boards disposed in a parallel configuration, the plurality of circuit boards being perpendicular to a longitudinal axis of the medical cable.

Certain embodiments provide a medical cable for transmitting data between a patient monitor and a sensor capable of detecting one or more physiological parameters of a patient. The medical cable may include a first connector configured to be coupled to the patient monitor and a second connector configured to be coupled to the sensor and to receive a sensor signal from the sensor that comprises information related to the one or more physiological parameters The medical cable may further include authentication circuitry configured to receive a test signal from the patient monitor and generate a ramp output signal responsive to the test signal that reaches a target voltage within an amount of time expected by the patient monitor. In certain embodiments, the patient monitor is configured to at least partially prohibit the transmission of data between the patient monitor and the sensor when the authentication circuitry fails to provide the output signal to the patient monitor at a set time after the sensor and the medical cable are physically connected.

Certain embodiments provide a method of authenticating a medical cable in a physiological parameter monitoring system. The method may include connecting the medical cable to a patient monitor, receiving a test signal with an authentication circuit disposed in the medical cable, converting the test signal into a substantially constant current signal, generating a ramp signal using the current signal, and providing the ramp signal to the patient monitor, thereby enabling the monitor to authenticate the medical cable.

In certain embodiments, the method further includes receiving a confirmation signal from the patient monitor indicating that the medical cable is in an authenticated state and using the medical cable, transmitting a sensor signal that comprises information related to one or more physiological parameters from a sensor to the patient monitor.

In certain embodiments, the method may include determining whether the monitor has authenticated the medical cable. When it is determined that the monitor has authenticated the medical cable, the method may include transmitting a sensor signal that comprises information related to one or more physiological parameters from a sensor to the patient monitor using the medical cable. When it is determined that the monitor has not authenticated the medical cable, the method may include at least partially prohibiting transmission of the sensor signal from the sensor to the patient monitor with the medical cable.

In certain embodiments, a medical cable for transmitting data between a patient monitor and a sensor includes a cable body, a first connector connected to the cable body and configured to be coupled to a patient monitor, and a second connector connected to the cable body. The second connector can be coupled to a sensor and to receive a sensor signal from the sensor. The medical cable can also include a safety switch that can be in electrical communication with the sensor. The safety switch can be in a first state when the second connector is coupled to the sensor and in a second state when the second connector is not coupled to the sensor, such that the safety switch prevents authentication of the cable to the patient monitor when the safety switch is in the second state.

In still other embodiments, a medical cable for transmitting data between a patient monitor and a sensor includes a cable body, a first connector connected to the cable body and configured to be coupled to a patient monitor, and a second connector connected to the cable body. The second connector can be coupled to a sensor and to receive a sensor signal from the sensor. The medical cable can also include a safety switch that can be in electrical communication with the sensor. The safety switch can be in a first state when the second connector is coupled to the sensor and in a second state when the second connector is not coupled to the sensor, such that the safety switch at least partially prevents the patient monitor from outputting a measurement value when the sensor is not connected to the second connector

BRIEF DESCRIPTION OF THE DRAWINGS

The components within the figures are not necessarily to scale, emphasis instead being placed upon clearly illustrating the principles of how certain embodiments disclosed herein may operate. Moreover, in the figures, like reference numerals designate corresponding parts throughout the different views.

FIG. 7A is a side view of an embodiment of a medical cable.

FIG. 7B is a perspective view of an embodiment of a sensor connector assembly for use in a medical cable.

FIG. 7C is a schematic diagram of an embodiment of the medical cable depicted in FIG. 7A.

DETAILED DESCRIPTION

Disclosed herein are various devices and methodologies for authenticating a medical cable for use in a patient monitoring system. For the purpose of description, it will be understood that the term authentication is used herein according to its broad and ordinary meaning and can include any validation, confirmation, or verification of compatibility or suitability of an electronic device. For the purpose of description, it will be understood that the terms authentication and verification can be used interchangeably, depending on the context of usage.

For the purpose of description, it will be understood that a medical cable, in addition to having its ordinary meaning, can include any device having an electrical conductor configured to facilitate the transmission of an electronic signal, such as between two or more devices. Non-limiting examples of such medical cables can include electronic cables for transmitting signals from medical sensor or transducer devices to a patient monitor. Non-limiting examples of such a medical cable can include one or more discrete devices such as resistors, capacitors, inductors, diodes, transistors, or other devices or circuits.

Authorization circuits and methods can be implemented in hardware, software, or a combination of hardware and software, and may provide analog and/or digital output signals. When implemented in hardware, as described herein, medical cable authorization can be implemented using hardware elements and/or logic. When authorization is implemented at least partially in software, the software portion can be used to control components in a patient monitoring system so that various operating aspects can be software-controlled. The software can be stored in a non-transitory state in a memory element or elements and executed by a suitable instruction execution system (e.g., a microprocessor) coupled to the memory.

Figure 1A:
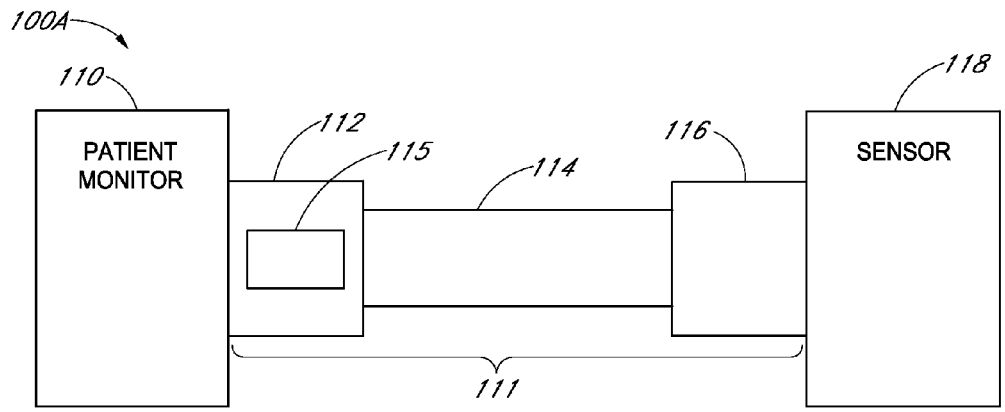
FIGS. 1A-1C depict block diagrams of embodiments of a patient monitoring system including a medical cable with an authentication circuit.
Figure 1B:
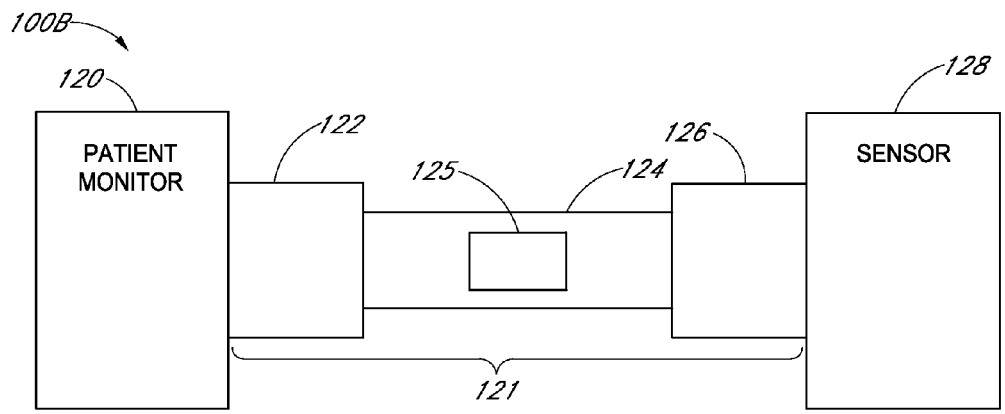
Figure 1C:
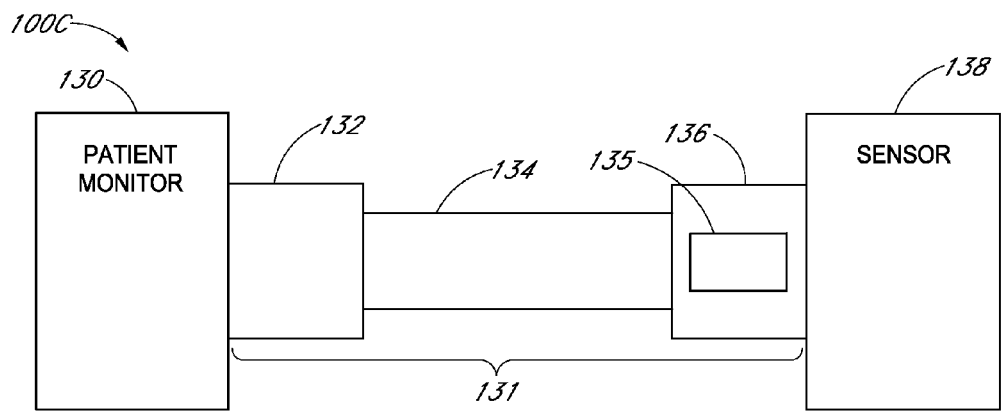

In accordance with an illustrative embodiment of a patient monitoring system, FIGS. 1A-1C depict block diagrams of patient monitoring systems (100A, 100B, 100C) including a medical cable assembly (111, 121, 131) with an authentication circuit (115, 125, 135). As shown in FIG. 1A, for example, patient monitoring system 100A includes a patient monitor 110 for receiving, processing, displaying, or otherwise interacting with data including information relating to one or more physiological parameters of a patient. In certain embodiments, the patient monitor includes a display screen for visually communicating information relating to a patient and/or the patient monitoring system 100A to a user.

The system 100A includes a medical cable 111 that has a monitor connector 112 that allows the patient monitor to communicate with the medical cable assembly 111. Monitor connector 112 may include a housing containing one or more structures or devices. The medical cable assembly 111 may allow for data and/or power communication using one or more wires and/or conductors that traverse at least a portion of a longitudinal axis of a body of the medical cable assembly 114. The medical cable assembly 111 may further include a sensor connector 116 that allows a sensor 118 to communicate with the medical cable assembly 111. Features of the sensor connector 116 are described in greater detail below in connection with FIGS. 7B and 7D. It may be desirable for parameter data to be provided to more than one monitor device. For example, with respect to blood pressure monitoring, it may be desirable to provide a signal to a standard patient monitor, as well as a cardiac output monitor. Therefore, cable assembly 111 may include more than one monitor connector. With respect to such a configuration, the cable assembly 111 or the sensor 118 can include a circuit to convert a sensor signal to a digital signal to reduce the risk or effect of signal loss or corruption when splitting to multiple monitors or for any other purpose.

The sensor 118 may be a digital sensor, an analog sensor, or a combination digital and analog sensor. Sensor 118 may be configured to detect one or more physiological parameters related to a patient and transmit a signal based at least partly on such parameters to the patient monitor 110, via medical cable assembly 111. For example, sensor 118 may be a transducer configured to convert physiological information into an electrical signal that can be transmitted and/or processed by a patient monitoring system to measure one or more physiological parameters. In certain embodiments, sensor 118 comprises a pressure transducer for detecting blood pressure. In certain embodiments, the sensor 118 is configured to detect one or more of the following parameters: blood pressure, heart rate, blood-oxygenation level, or another physiological parameter. For example, sensor 118 may include a pressure cuff or catheter for detecting blood pressure in a patient. More generally, the sensor 118 can be a noninvasive, invasive, or minimally-invasive sensor.

In direct, or invasive, blood pressure monitoring systems, a catheter may be inserted into a patient's circulatory system with the end of the catheter having an opening to the blood stream, typically in a major or peripheral blood vessel. First, a needle is inserted into a peripheral blood vessel. For example, if it is desired to monitor arterial blood pressure, the needle may be inserted into the radial artery. If, on the other hand, venous blood pressure is to be monitored, the needle may be inserted into the antecubital, radial, jugular, or subclavian veins. Once the needle is properly inserted, a special catheter is threaded through the needle and into the blood vessel until the tip of the catheter is positioned at the particular point within the body at which it is desired to make the blood pressure measurement. Then, with the catheter in place, the needle may be withdrawn.

An I.V. set attaches to the proximal end of the catheter protruding from the patient so that a solution flows through the catheter and into the patient. The I.V. solution provides a fluid "column" through which pressure pulses are transmitted, and a pressure transducer positioned along the fluid column monitors those pressure pulses. Generally, the pressure transducer consists of a dome that functions as a reservoir for the I.V. fluid. The dome includes a resilient diaphragm that attaches to an electrical transducer. The transducer senses pressure fluctuations in the diaphragm and converts them into electrical signals which then transmit through a cable to a monitor for amplification and display. In modern systems a single silicon chip can comprise both the pressure diaphragm and the measuring circuitry of the pressure transducer. Since such silicon chips can be relatively cheaply mass-produced, the total cost of pressure transducers is reduced to the extent that the transducer becomes economically disposable. The cable includes a connector so that the transducer and associated portion of the cable can be discarded after use, whereas the mating connector and cable hard-wired to the monitor can be reused. Such disposable blood pressure transducers are the standard of care in the OR, ICU or CCU.

The patient monitoring system 100A of FIG. 1A also includes a cable authentication module 115. In certain embodiments, such as that depicted in FIG. 1A, the cable authentication module 115 is disposed at least partially within, or connected to, monitor connector 112, such as within a housing of the monitor connector. In certain embodiments, the patient monitor 110 is configured to communicate with cable authentication module 115. For example, the patient monitor 110 may send a test signal that is received by cable authentication module 115, and receive a corresponding signal from cable authentication module 115 relating to whether medical cable assembly 111 is an expected, or authentic/compatible cable. Communication between the medical cable assembly 111 and the patient monitor 110 may comprise an analog or digital handshake or partial handshake between the two devices. Portions of cable authentication module 115 may be located at various distinct locations of the cable. For example, portions of the cable authentication module 115 can be located in one or both of the connectors 112, 116 and/or the cable body 114. The authentication module may instead be entirely contained within a single region of the medical cable assembly 111, for example, as shown in FIGS. 1A-1C.

The patient monitoring system 100A may be configured such that the patient monitor 110 communicates with cable authentication module 115 in order to confirm authenticity of the medical cable assembly 111. In certain embodiments, if the patient monitor is unable to confirm compatibility or authenticity of the medical cable assembly 111 by communicating, directly or indirectly, with cable authentication module 115, the patient monitor 110 can at least partially prohibit communication between the patient monitor 110 and medical cable assembly 111 and/or sensor 118. In other embodiments, when the patient monitor is unable to confirm compatibility or authenticity of the medical cable assembly 111, the patient monitor receives, or continues to receive, a signal from the medical cable assembly 111, but outputs an error message of some kind to indicate the incompatibility.

In the embodiment depicted in FIG. 1B, cable authentication module 125 is at least partially disposed within, or connected or in proximity to, a body portion 124 of medical cable assembly 121. For example, a rigid housing may be attached to a portion of the cable body 127 such that one or more wires disposed within an outer sheath of the cable body 127 can communicate with one or more devices disposed at least partially within the housing. Such devices may include discrete circuit components and/or IC chips disposed, for example, on a circuit board or other substrate. The patient monitor 120 may communicate with cable authentication module 125 over one or more conductive wires running between the cable authentication module 125 and the patient monitor 120. Cable authentication module 125 may be located at, or in proximity to, any suitable location or position along the cable body 124. In certain embodiments, cable authentication module 125 is disposed at or near a portion of the cable body that is relatively close to the monitor connector 122. In certain embodiments, cable authentication module 125 may be disposed at or near a portion of the cable relatively close to a sensor connector 126 that is configured to be connectable to a sensor 128. The sensor connector 126 may be located at or near a distal end of cable body 124 with respect to the monitor connector 122.

Figure 10:
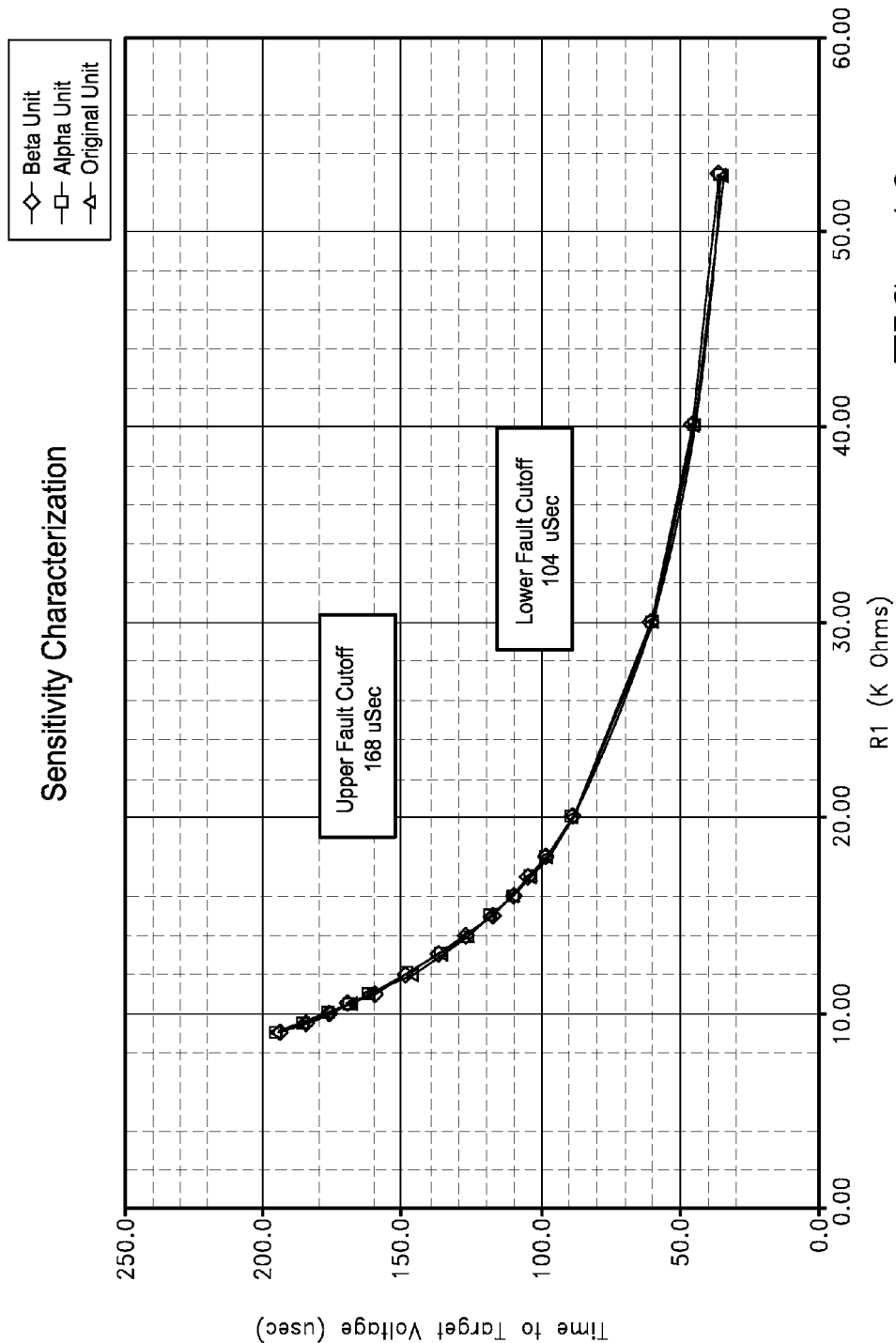
FIG. 10 is a graph showing the time it takes an output voltage signal of an embodiment of an authentication circuit to reach a target voltage with respect to a resistance value associated with the authentication circuit.

In the embodiment depicted in FIG. 10, cable authentication module 135 is at least partially disposed within, or connected or in proximity to, sensor connector 136. For example, sensor connector 136 may include a rigid housing such that one or more wires disposed within the housing can communicate with one or more devices disposed at least partially within the housing. Such devices may include discrete circuit components and/or IC chips disposed, for example, on a circuit board or other substrate.

In certain embodiments, a patient monitoring system similar to those discussed above may include at least a portion of an authentication circuit in a sensor as opposed to, or in addition to, an authentication circuit disposed within, or connected to, a medical cable. Furthermore, at least a portion of an authentication circuit could be included in a patient monitor instead of, or in addition to, other locations in a patient monitoring system.

Figure 2:
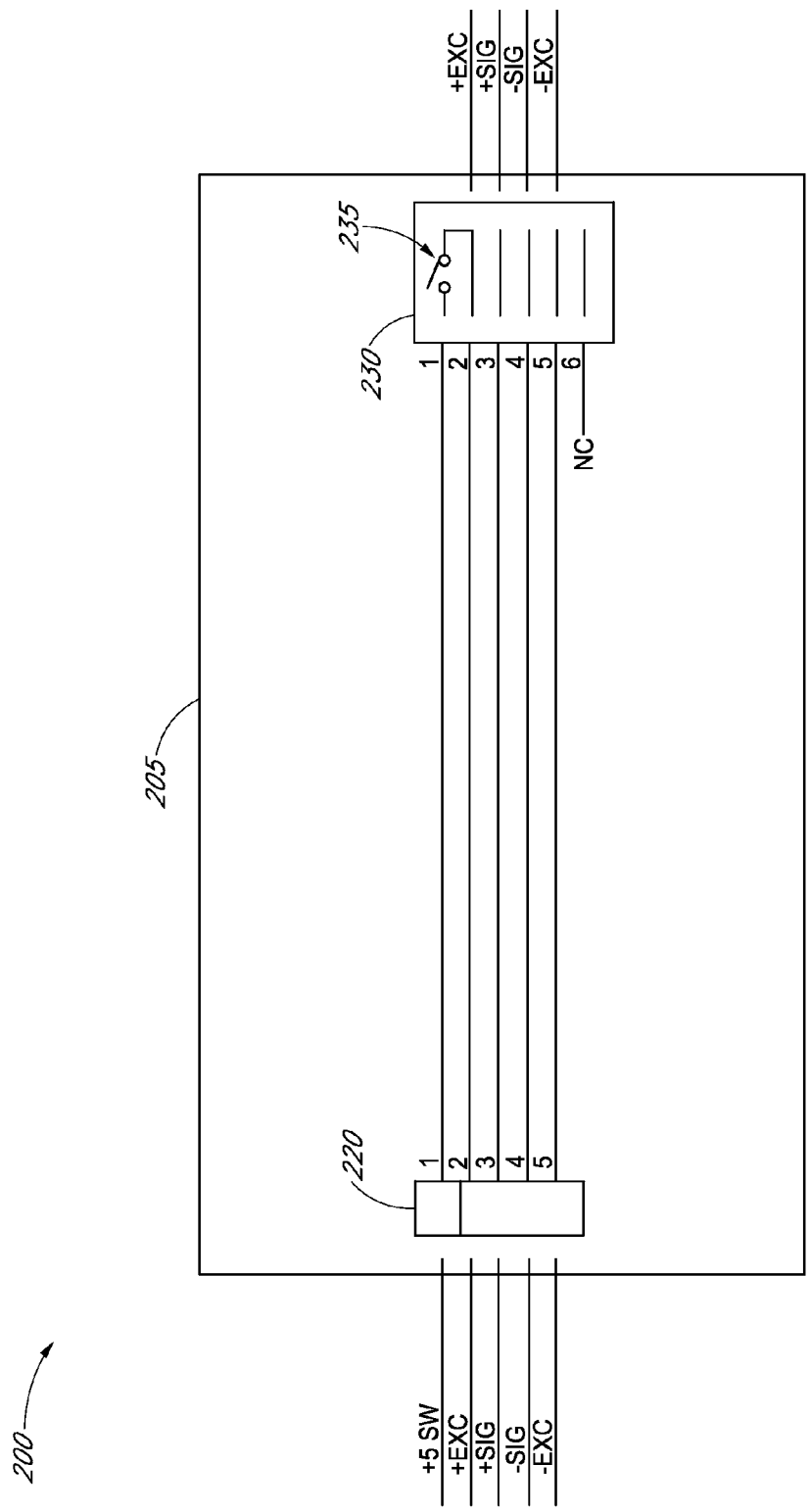
FIG. 2 is a schematic diagram of an embodiment of an electronic circuit that may be used in a patient monitoring system.

FIG. 2 depicts a schematic diagram of an embodiment of an electronic circuit 205 that may be used in certain embodiments disclosed herein. The electronic circuit 205 may be disposed in or connected to a portion of any of the medical cable assemblies described above. In certain embodiments, the electronic circuit 205 receives one or more electrical signals at a header portion 220, or at switch module 230, which are identified, for convenience only, as +5 SW, +EXC, +SIG, −SIG, and −EXC. For example, +EXC may refer to a positive test voltage signal or excitation signal from a patient monitor; −EXC may refer to a common potential line; and +SIG and −SIG may refer to signal lines (e.g., differential lines) for sending a signal from the sensor to the monitor. In certain embodiments, such signals are received via electrical connecting pins in contact with one or more wires. Conductive paths 1, 2, 3, 4, and 5 allow for transmission of signals between an optional switch module 230 and header module 220.

As shown in FIG. 2, switch module 230 includes a safety switch 235 in series between conductive paths 1 and 2. The switch module may be connected to a sensor, wherein connecting the switch module 230 to the sensor can cause the switch 235 to be closed and/or disconnecting the switch module 230 from the sensor can cause the switch 235 to be opened. In certain embodiments, switch module 230 receives an electronic signal on conductive path 2, such as a direct-current voltage signal, and redirects at least a portion of the signal towards header module 220 via conductive path 1 when switch 235 is in a closed state. When switch 235 is in an open state, as depicted in FIG. 2, substantially none of the signal on line 2 is redirected to line 1 in one embodiment.

It may be desirable to prevent authentication of a medical cable assembly under certain circumstances in view of potential safety concerns. For example, some monitors may output measurements if a medical cable assembly is connected to such a monitor, even if a sensor is not connected to the medical cable. Further, if a medical sensor is not properly connected to a cable, measurements presented by the patient monitor to a clinician or other attendant may be inaccurate and/or misleading. Advantageously, in certain embodiments, the safety switch 235 acts as a safety mechanism to at least partially prevent the patient monitor from picking up or reading invalid measurements when a sensor is not connected or is connected improperly. The safety switch 235 can therefore reduce the risk that an incorrect evaluation of a patient's health will be made due to erroneous measurements.

In certain embodiments, when a sensor is not connected or is not properly connected to the electronic circuit 205, the switch 235 is in an open state. In this open state, the safety switch 235 can prevent power from being provided to an authentication circuit (see, e.g., FIG. 4). In another embodiment, the safety switch 235 prevents or at least partially prevents measurement current from being transmitted by the medical cable assembly to a patient monitor when in an open state. The safety switch 235 closes in one embodiment when a sensor is properly connected to the switch 235, thereby allowing power or current to pass to an authentication circuit (see FIG. 4). The switch 235 may be a contact switch (such as a pushbutton switch), a rocker switch, or another type of switch. The switch 235 can be a semiconductor switch in some embodiments, such as a diode, transistor or MOSFET, or any combination of the same. Accordingly, the switch 235 can high-enabled or low-enabled. In a low-enabled state, the switch 235 can allow power or current to be provided to an authentication circuit disposed in the cable when the switch 235 is open.

In certain embodiments, a voltage signal +EXC is received by the connector 236 and transmitted along conductive path 2. The signal is further redirected within the switch module 235 and output. Such signal, identified by reference +5 SW in FIG. 2, may be provided to an authentication module to facilitate the functionality thereof. The electronic circuit 205 may further relay one or more signals (e.g., +EXC, +SIG, −SIG, −EXC), or modified versions thereof, to or from a sensor.

Figure 3:
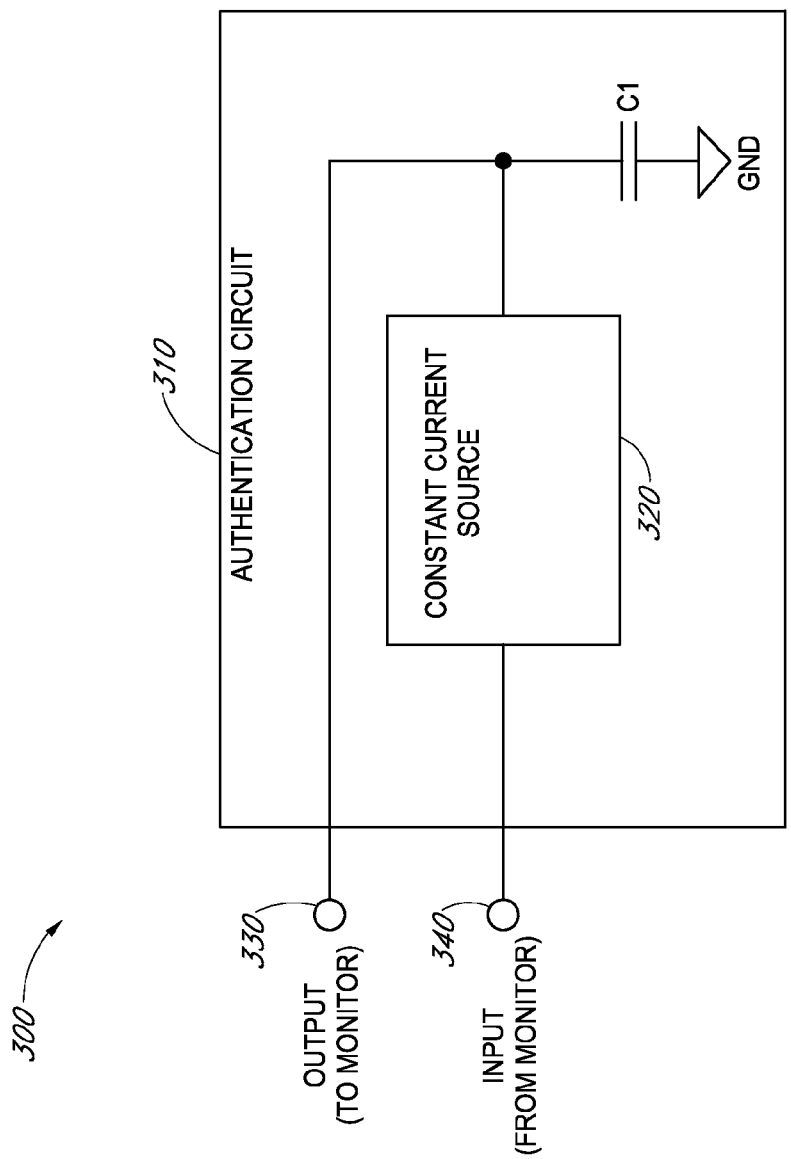
FIG. 3 depicts a block diagram of an embodiment of an authentication circuit for use in connection with a medical cable in a patient monitoring system.

FIG. 3 depicts a block diagram of an embodiment of an authentication module or circuit 310 for use in connection with a medical cable in a patient monitoring system, such as any of the cables and systems described herein. The depicted embodiment of the authentication circuit 310 includes an input port 340 and an output port 330. In certain embodiments, both input 340 and output ports 330 may be connected to a patient monitor (not shown). Further, authentication circuit 310 may include one or more additional ports that may be, for example, connected to a patient sensor, or elsewhere. The authentication circuit 310 can include a constant current source 320 and a capacitor C1, in addition to possibly other devices or components (as described below). In certain embodiments, authentication circuit 310 provides a signal to the monitor that can enable the monitor to determine whether the cable containing the authentication circuit 310 is a valid cable.

The authentication circuit 310 can provide a ramp voltage signal to the output port 330, wherein the voltage of the signal reaches a certain value at after a period of time expected by the monitor. The ramp signal can have a linear slope or the like. In one embodiment, the ramp signal is a sawtooth waveform, or at least one period of a sawtooth waveform, or a portion thereof. In another embodiment, the ramp signal is a reverse sawtooth waveform, or a portion thereof. In yet another embodiment, the ramp signal is at least a portion of a triangle waveform. The ramp signal may or may not be periodic. In certain embodiments, the authentication circuit 310 receives a voltage signal from a patient monitor via input 340. The authentication circuit 310 may use at least a portion of the voltage signal to drive a constant current source, which, in turn, provides a substantially constant current to capacitor C1. Charging a capacitor with a constant current can produce a linearly increasing voltage across the capacitor over time because the capacitor can integrate the constant input to produce a ramp output. The output of the authentication circuit 310 to the output port 330 can be in electrical communication with the capacitor, such that the output signal is based on the voltage across the capacitor C1. Therefore, the output port 330 may provide a ramp signal to the patient monitor.

The current source 320 and/or capacitor C1 may be substituted or supplemented with one or more other components or devices configured to receive a signal from the monitor and produce a ramp voltage signal, such as a ramp signal having predetermined response characteristics. For example, the authentication circuit 310 may include a transimpedance amplifier connected to the current source 320 to convert the current output from current source 320 into a voltage output. Further, output from the transimpedance amplifier may be supplied to an integrator circuit instead of, or in addition to, a capacitor. The output from the integrator circuit may provide a ramp voltage signal suitable for certain patient monitor authentication testing.

In another embodiment, input 340 is provided to an integrator circuit, instead of to current source 320 and capacitor C1, which may provide a suitable ramp voltage output. Furthermore, in certain embodiments, the authentication circuit 310 may include one or more timer circuits, such as a multivibrator circuit (e.g., a 555 or 556 timer), in addition to, or in place of components shown in FIG. 3, which are configured to provide desirable output signals expected by the patient monitor. Other examples of circuit components that may be included in authentication circuit 310 in place of, or in addition to, one or more other components described herein include one or more function generator circuits, oscillator circuits, resistor networks (such as a resistor ladder), a processor that outputs a ramp or other suitable waveform, or other circuit configured to provide a desirable output signal for purposes of demonstrating authenticity or compatibility of a medical cable assembly.

Figure 4:
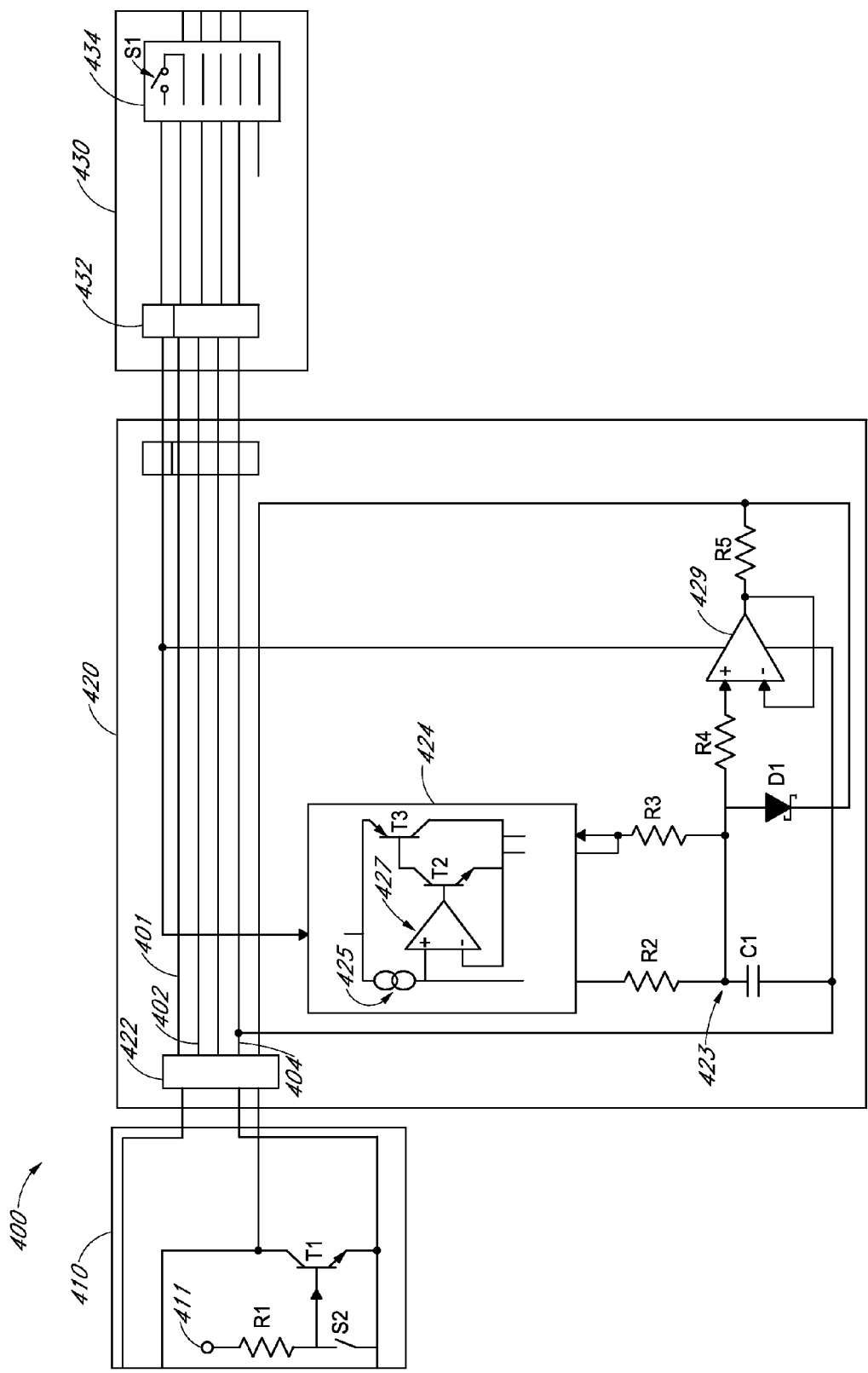
FIG. 4 is a schematic diagram of an embodiment of a patient monitoring system including a medical cable authentication circuit.

FIG. 4 illustrates a schematic diagram of an embodiment of a patient monitoring system 400 having a medical cable authentication circuit 420. The circuit in FIG. 4 is identified in three regions: a patient monitor circuit 410, an authentication circuit 420, and a switch circuit 430. However, it should be understood that circuitry described in connection with FIG. 4 can be located in any of the depicted regions, or in any suitable location in the patient monitoring system 400.

In certain embodiments, the patient monitor circuit 410 includes a transistor T1, the base or gate of which is connected in parallel to a resistor R1 and a switch S2. The patient monitor (not shown), such as the 110 may be configured to provide a test signal, such as a direct-current voltage signal, or pulse signal, to connector 422, for example, a 4.2-Volt DC signal, a 5 V signal, or some other voltage value. The test signal from the patient monitor may be transmitted within the cable circuit along conductive path 402. At least a portion of the test signal may be directed to the switch circuit 430 and pass through a connector or header portion 432 and enter switch module 434. Switch module 430, as described above with respect to FIG. 2, may be configured to redirect at least a portion of the test signal back to the authentication circuit 420 via switch S1, where it is provided to one or more components of the authentication circuit 420 over conductive path 401. In certain embodiments, a test signal is provided from the patient monitor to one or more components of the cable circuit 420 without being directed to switch circuit 430. In certain embodiments, conductive line 404 is tied to a common potential, which may be a ground potential.

In certain embodiments, when the switch S1 is in a closed state, the switch passes power to the cable circuit 420, allowing the authentication circuit 420 to authenticate the cable. In an open state, the switch S1 prevents or substantially prevents power from reaching the authentication circuit 420, thereby preventing the cable from authenticating to the monitor. As a result, the switch S1 can at least partially prevent the monitor from outputting measurements in response to detecting the authentication of the cable when a sensor is not present or not properly connected.

In certain embodiments, the test signal drives a current source 424. In one embodiment, the current source 424 is optionally programmable. The current source 424 may be an integrated circuit. For example, current source may be a 2-terminal programmable current source, such as, for example, the model LT3092 current source manufactured by Linear Technology Corporation of Milpitas, Calif. See LT3092 Datasheet, available at http://cds.linear.com/docs/Datasheet/3092fb.pdf (hereinafter, "the LT3092 datasheet"), which is hereby incorporated by reference in its entirety. As described in the datasheet, the current source 424 can include at least an internal current source 425, an amplifier 427, and transistors T2 and T3, which are configured to amplify the current of current source 425. In certain embodiments, current source 425 is an approximately 10 µA source, and the amplification provided by the programmable current source 424 is based on the values of resistor R2 and R3 connected thereto, wherein the current source produced current in the range of, for example, about 1-5 mA, or about 0.1 mA to about 10 mA, or some other value.

As described above, the current source 424 may output a substantially constant current that the capacitor C1 converts into a ramp signal. Line 401 of the authentication circuit 420 may be connected to an input pin (pin 3) of the current source 424. The resistor R2 may be connected to a SET pin (pin 1), while resistor R3 may be connected to output pins (pins 2 and 4) of the current source 424. In the LT3092 datasheet, the R2 resistor is referred to as "$R_{SET}$" and the R3 resistor is referred to as "$R_{OUT}$". See id., p. 8. The resistors R2 and R3 can tune the current source 424 to program the value of the output current. The current flowing into the capacitor C1 from Node 423 in FIG. 4 can be related to the output current defined by the LT3092 datasheet in the following equation (1) or the like:

$$I_C = I_{SOURCE} = 10 \mu A \cdot \frac{R_{SET}}{R_{OUT}}. \tag{1}$$

where $I_{SOURCE}$ is the output current. With values of R1 being 13.0 kΩ and R2 being 100Ω, the current supplied from Node A to the capacitor can therefore be, in some embodiments, about 1.30 mA.

It may be possible to effectively modify the current from programmable current source 424 by modifying the values of resistors R2 or R3, or both. In certain embodiments, resistor R2 has a value in the range of approximately 2 to 5 K Ohms, or between 11 K Ohms and 17 K Ohms. For example, R2 may have a value of approximately 2.1 K Ohms or 4.2 K Ohms in order to produce a desirable output signal. In certain embodiments, R2 has a value of approximately 13 K Ohms. Furthermore, capacitor C1 may have a value of approximately 0.01 µF to 0.09 µF. For example C1 may have a value of approximately 0.082 µF or 0.085 µF in order to produce a desirable output signal. In other examples, capacitor C1 may have a value of around 0.1 µF or more, or any value in a range of about 0.05 µF to about 0.15 µF, or some other range. However, it should be understood that capacitor values may vary substantially from system to system, and such values are provided herein as examples only. Any suitable value may be implemented in accordance with embodiments disclosed herein.

Adequacy of the output signal of authentication circuit 420 may be measured by the amount of time the authentication circuit 420 takes to produce one or more suitable output voltage signals in response to receiving an input test signal. For example, it may be desirable for an input voltage signal to reach a target voltage level or have a pulse width within a predefined range. The target time in which the target voltage level is reached can be any period of time. However, some examples of time periods include about 100 µS to about 200 µS, or about 500 nS to about 50 µS, or about 50 µS to about 300 µS, or about 300 µS to about 1 mS, or about 1 mS to about 100 mS. In certain embodiments, a desirable pulse width is in the range of 80 µS to 160 µS. For example, the desirable pulse width may be 110, 135, 138, or 150 µS, or another value. The capacitance value of C1 and/or the resistance value of R2 may be manipulated to achieve a desirable pulse width as described above.

In the depicted embodiment, the authentication circuit 420 includes a buffer amplifier 429, which may be connected to one or more resisters R4, R5. In other embodiments, the buffer amplifier 429 and/or one or more of resistors R4 and R5 can be omitted from the authentication circuit 420. However, the buffer amplifier 429 can reduce any loading by the monitor circuit 410 on the authentication circuit 420.

Authentication circuit 420 may also include a clamping diode D1, which can shift the DC value of the output signal of the buffer amplifier 429. For example, the diode D1 may be configured such that an approximately 100 mV to 300 mV drop appears across the diode D1, or about a 100 mV to 600 mV drop. However, diodes having values greater or less than such range may be incorporate as desirable, or suitable in the system 400. Among possibly other things, the diode D1 may be configured to discharge, or drain voltage on the capacitor C1, such as between test cycles of the patient monitoring system 400. In one embodiment, the diode D1 is a Schottky diode, although other types of diodes can be used in place of a Schottky diode. In certain embodiments diode D1 is replaced by, for example, an operational amplifier or other device through which capacitor C1 can discharge. In certain embodiments, the diode D1 and/or the conductive branch on which it lies may be omitted from authentication circuit 420. Various other components may be omitted from authentication circuit 420, such as, for example, resistors R2, R3, and R4.

In certain embodiments, the buffer amplifier 429 has a unity gain or approximately unity gain. Therefore, the authentication circuit 420 effectively outputs the ramp signal generated by the current source 424 and capacitor C1, and clamped by diode D1, to the patient monitor circuit 410. However, the buffer amplifier can have a gain other than unity in some embodiments.

Figure 5:
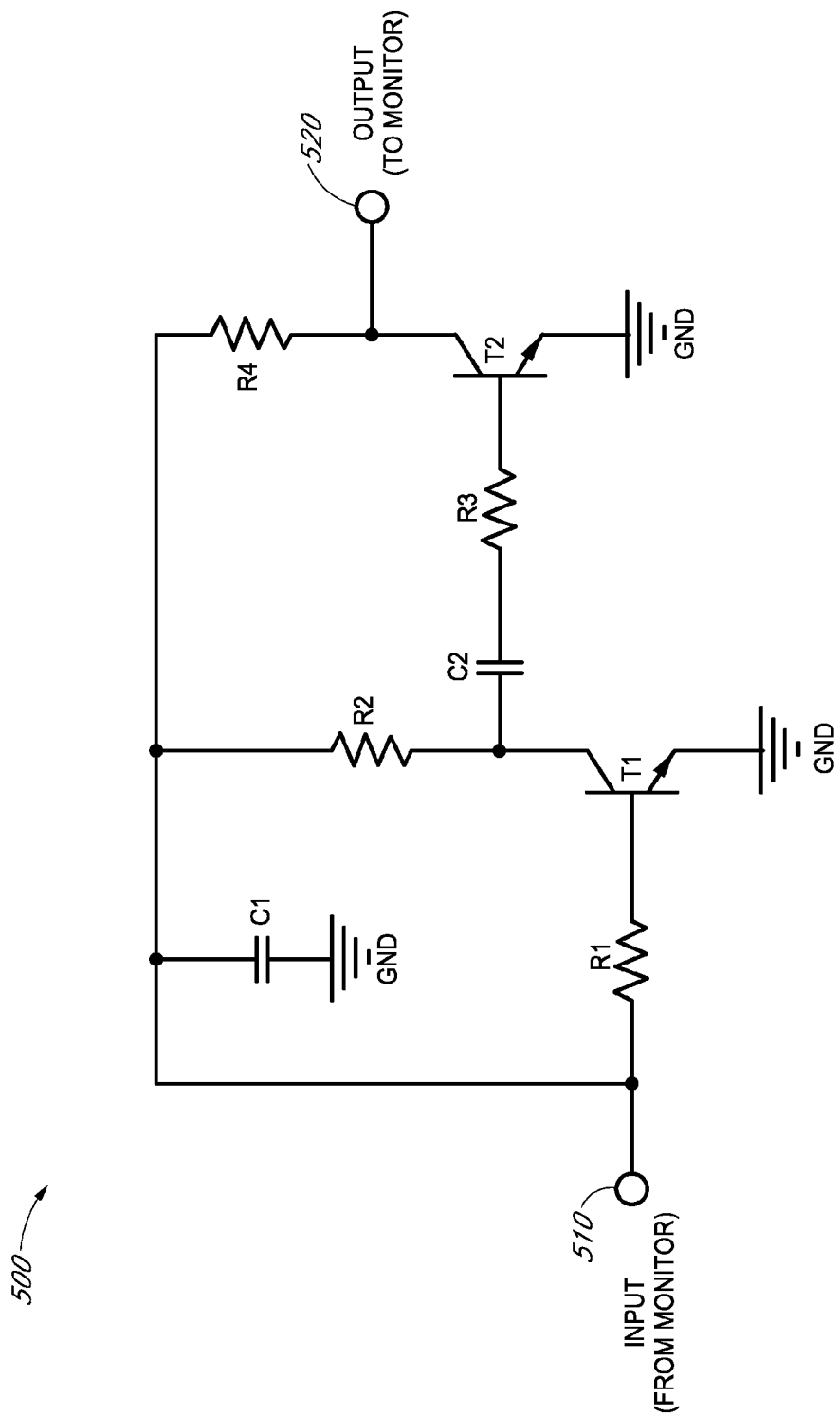
FIG. 5 is a schematic diagram of an embodiment of authentication circuit for use in connection with a medical cable in a patient monitoring system.

FIG. 5 provides a schematic diagram of an embodiment of an authentication circuit 500 for use in connection with a medical cable in a patient monitoring system. For example, authentication circuit 500 can be used in place of authentication circuit 420 described above with reference to FIG. 4. In certain embodiments, the authentication circuit 500 includes an input port 510 for receiving an electronic signal. For example, the authentication circuit may receive a test signal, such as, e.g., a direct-current voltage signal, from a patient monitor or other device. The authentication circuit 500 may be configured to generate an output signal to output port 520 based at least in part on the input signal. In certain embodiments, the output signal is an exponential voltage signal.

The authentication circuit 500 includes three resistors R1, R2, R3, and a capacitor C1 in a parallel configuration with respect to the input port 510. A transistor, such as, for example, a bi-polar junction transistor (BJT), is connected at its base to resistor R1 and at its collector to the parallel branches of resistor R2 and capacitor C2. Resistors R1 and R2 may serve to bias transistor Transistor T2 is connected at its base to resistor R3, which is in series with capacitor C2, while its collector is connected to resistor R4, and also provides the output signal to output port 520. Both transistors T1 and T2 may be tied to ground at their emitter.

A signal is input from a patient monitor at port 510, and is subsequently passed and/or amplified by T1 to the RC pair including capacitor C2 and resistor R3, which produce an exponential output signal having an RC time constant. The output of the RC pair is amplified by transistor T2 to produce an output signal. Because of the amplification of the T1 and/or T2 transistors, the rise time of the output waveform can differ from the rise time of the RC circuit between T1 and T2.

Figure 6:
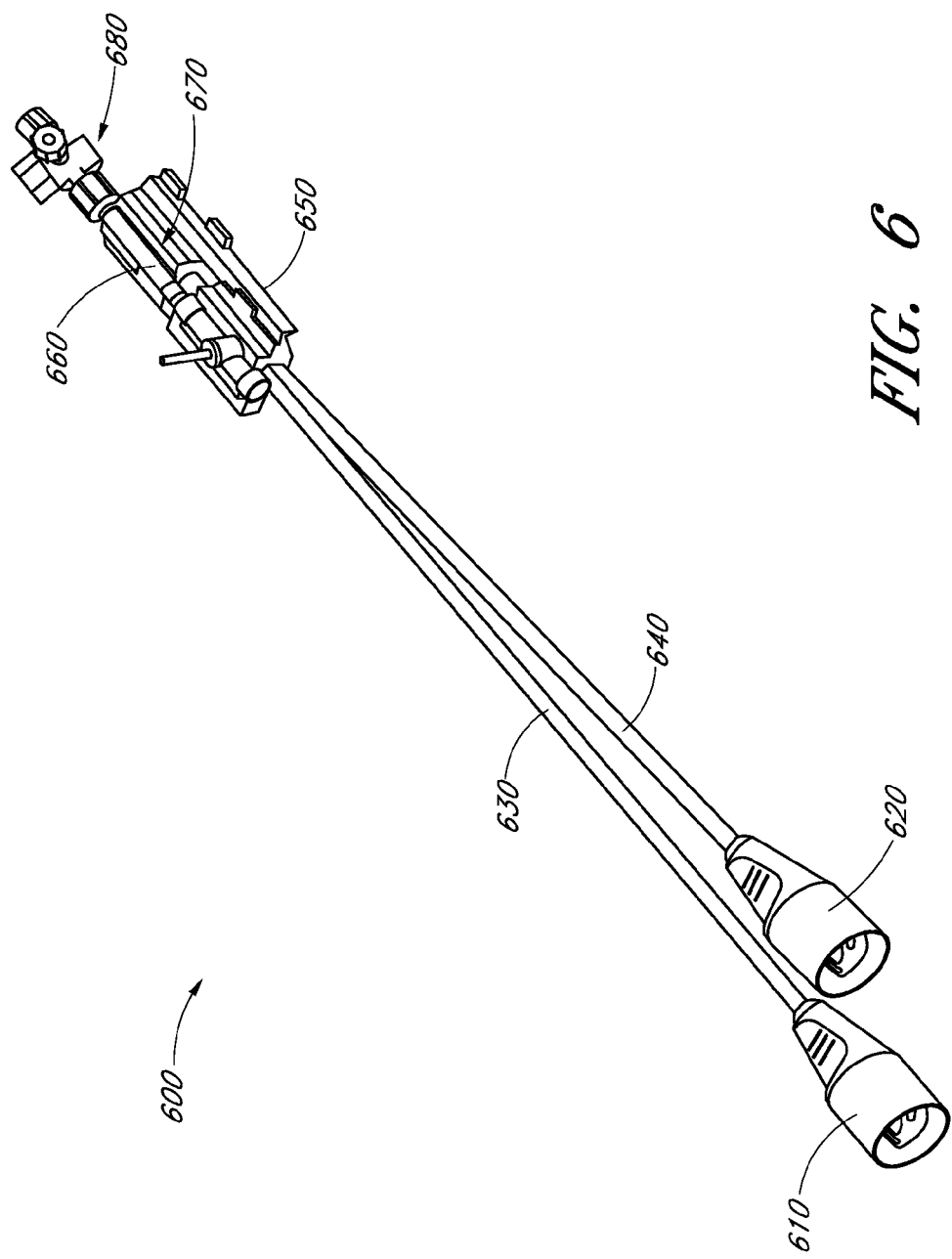
FIG. 6 is a perspective view of an embodiment of a sensor assembly for use in a patient monitoring system.

FIG. 6 is a perspective view of an embodiment of a sensor assembly 600 for use in a patient monitoring system. Sensor assembly 600 may be mountable to a mounting bracket and/or support pole (not shown) for use in a patient monitoring system. In certain embodiments, the sensor assembly 600 includes a housing 670 and one or more cables 630, 640. The cables 630, 640 may extend from one end of the housing 670 and terminate at one or more electrical connectors 610, 620. The sensor assembly 600 may further include a stopcock assembly 680, such as a two-port stopcock assembly, as shown, at a distal end of the housing 670. In certain embodiments, the sensor assembly 600 has a length of about 25-35 cm. However, the sensor assembly 600 may be any suitable length. In certain embodiments, an internal flow channel in the stopcock assembly 680 leads to a tube 660 disposed on the housing 670 opposite a mounting plate 650. The mounting plate 650 may engage a mounting bracket such that the tube 660 faces outward from the mounting bracket.

The sensor assembly 600 may be configured to be connected to various other components or devices. For example, a patient monitor may include cables and/or connectors that mate with the connectors 610, 620 and receive electrical signals indicative of one or more physiological parameters, such as, e.g., blood pressure detected using the sensor assembly 600. In certain embodiments, a catheter disposed in contact with a fluid to be measured may attach to a port of the stopcock assembly 680. In certain embodiments, multiple catheters may be used for pressure monitoring.

FIG. 7A is a side view of an embodiment of a medical cable assembly 700A having a monitor connector portion 710, a cable body portion 720, and a sensor connector portion 730. Monitor connector 710 is configured to be connectable to a patient monitor, while sensor connector 730 is configured to be connectable to a sensor that detects one or more physiological parameters of a patient. Cable body 720 may allow for transmission of signals between monitor connector 710 and sensor connector 730.

In certain embodiments, the sensor connector 730 comprises a housing containing at least a portion of one or more internal electrical components. FIG. 7B shows an exploded view of an embodiment of a connector assembly 732 that may be disposed at least partially within sensor connector 730. Connector assembly 732 may include a rigid structure 738 that, in certain embodiments, has a shape and configuration similar to that of a telephone jack. Rigid structure 738 may include one or more pins that are configured to couple to corresponding pins in a sensor assembly. Such pins may extend through rigid structure 738 and protrude through an outer surface of rigid structure 738. Such protruding pins are identified in FIG. 7B by reference number 739. Pins 739 may be configured, as shown, to penetrate one or more electronic circuit boards 734, such as by being threaded through holes in one or more of circuit boards 734.

Figure 7D:
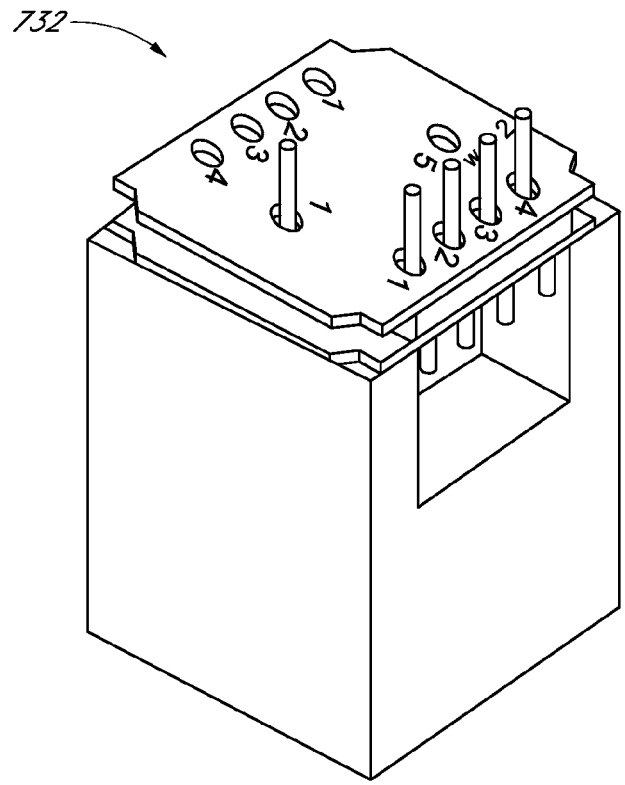
FIG. 7D provides a perspective view of an embodiment of an assembled connector assembly as depicted in FIG. 7B.

Electronic circuit boards 734 may include a medical cable authentication circuit as discussed above with respect to various embodiments. In certain embodiments, electronic circuit boards are configured to be placed adjacent to a rigid structure 738 in a stacked configuration, whereby pins 739 penetrate the circuit boards such that one of the circuit boards 734 is disposed in closer proximity to the surface of the rigid structure 738 than another circuit board. In addition, connector assembly may include a connector, or header member 736 disposed between the circuit boards 734 that includes electronic pins for electrically coupling the circuit boards 734. Header member 736 may also include a spacing structure for providing a desirable amount of space between the circuit boards 734. FIG. 7D provides a perspective view of an assembled connector assembly shown in FIG. 7B.

FIG. 7C illustrates a schematic diagram of the medical cable assembly depicted in FIG. 7A. FIG. 7C provides alternate views of various components discussed above in connection with FIGS. 7A and 7B, such as the monitor connector 710, the cable body 720, the circuit boards 734, the header member 736, and the rigid structure 738. The illustrated lines connecting between the various components of the medical cable assembly demonstrate the electrical connectivity between the various components.

Figure 7E:
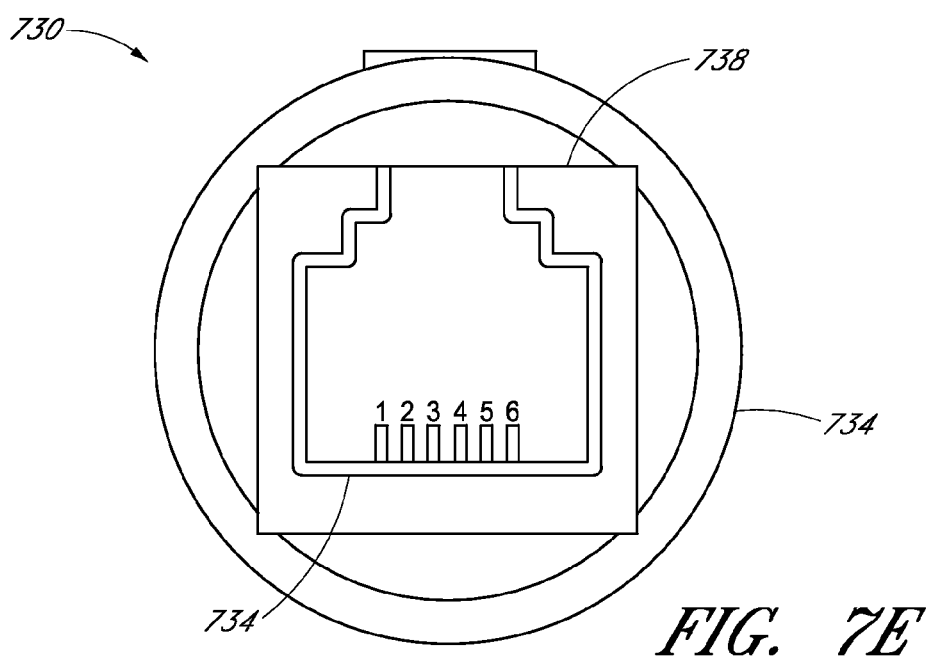
FIG. 7E provides an elevation view of an embodiment of an assembled connector assembly as depicted in FIG. 7B.

FIG. 7E shows a front view of a distal end of the sensor connector portion 730 depicted in FIG. 7A and described above. The connector portion 730 may include a cylindrical or other-shaped outer portion 734, which encases rigid structure 738. In certain embodiments, the rigid structure 738 includes a cutout interior engagement cavity 734 for accepting an electrical connector. The cavity 734 may be the same as or similar to a cavity of a standard telephone or Ethernet jack.

Figure 8:
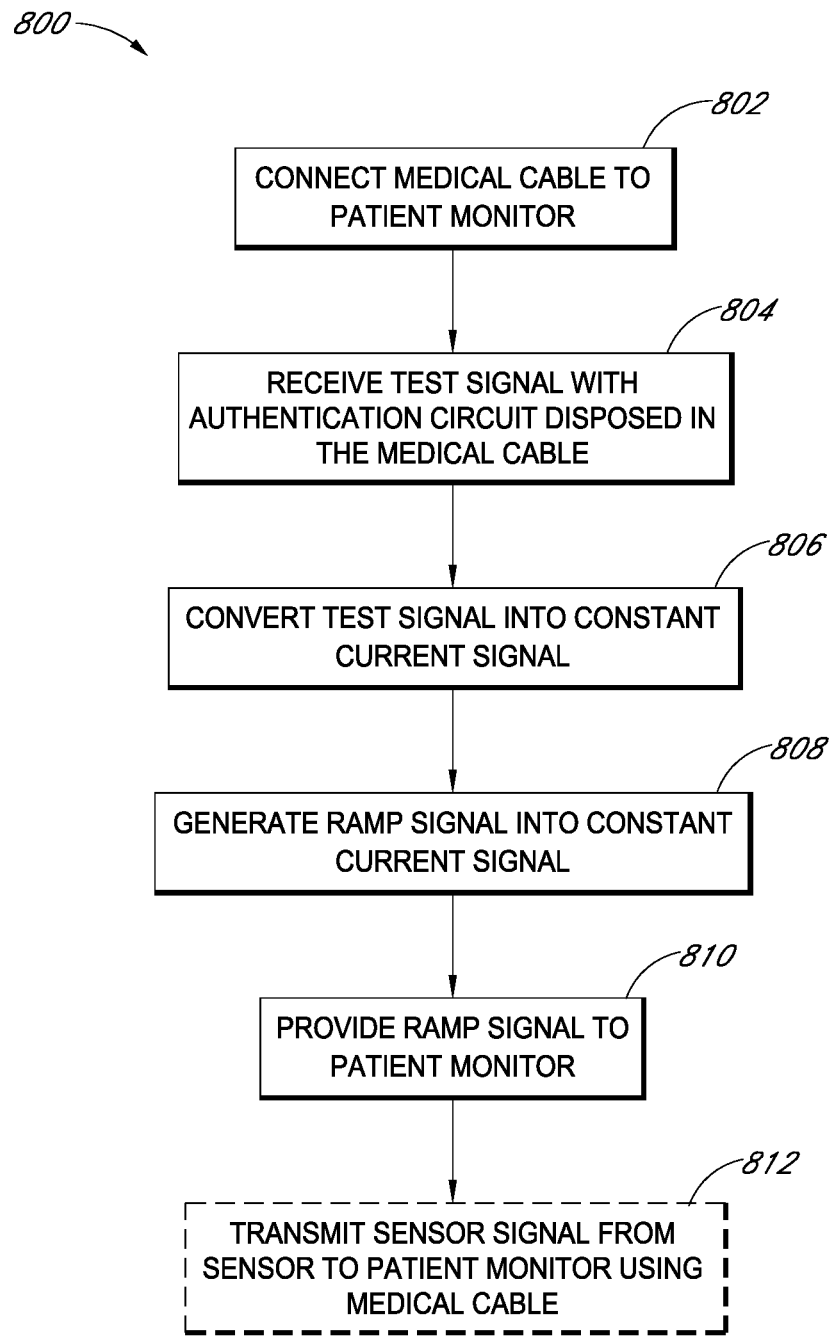
FIG. 8 is a flow chart depicting an embodiment of a method of authenticating a medical cable in accordance with aspects of the present disclosure.

FIG. 8 is a flow chart depicting a method 800 of authenticating a medical cable in accordance with one or more embodiments described herein. The method 800 may include connecting a medical cable to a patient monitor, as shown at block 802. For example a user may physically couple a medical cable to a patient monitor in any suitable manner, depending on the specifications of the system. At block 804, a test signal is received, such as from a patient monitor. The test signal may comprise a square pulse wave, a constant voltage signal, or any other signal. The test signal is received by an authentication circuit disposed in, or connected to, the medical cable. At block 806, the authentication circuit at least partially converts the test signal into a substantially constant current signal and, using at least a portion of such signal, generates a ramp output signal (block 808). At block 810, the ramp signal is provided to a patient monitor. In certain embodiments, the patient monitor may determine whether the medical cable is an authenticated cable based at least in part on the ramp signal. At block 812, a sensor signal is transmitted from the sensor to the patient monitor using the medical cable. In certain embodiments, the sensor signal may not be transmitted to the patient monitor, such as, for example, when it is determined that the medical cable is not an authenticated medical cable.

Figure 9:
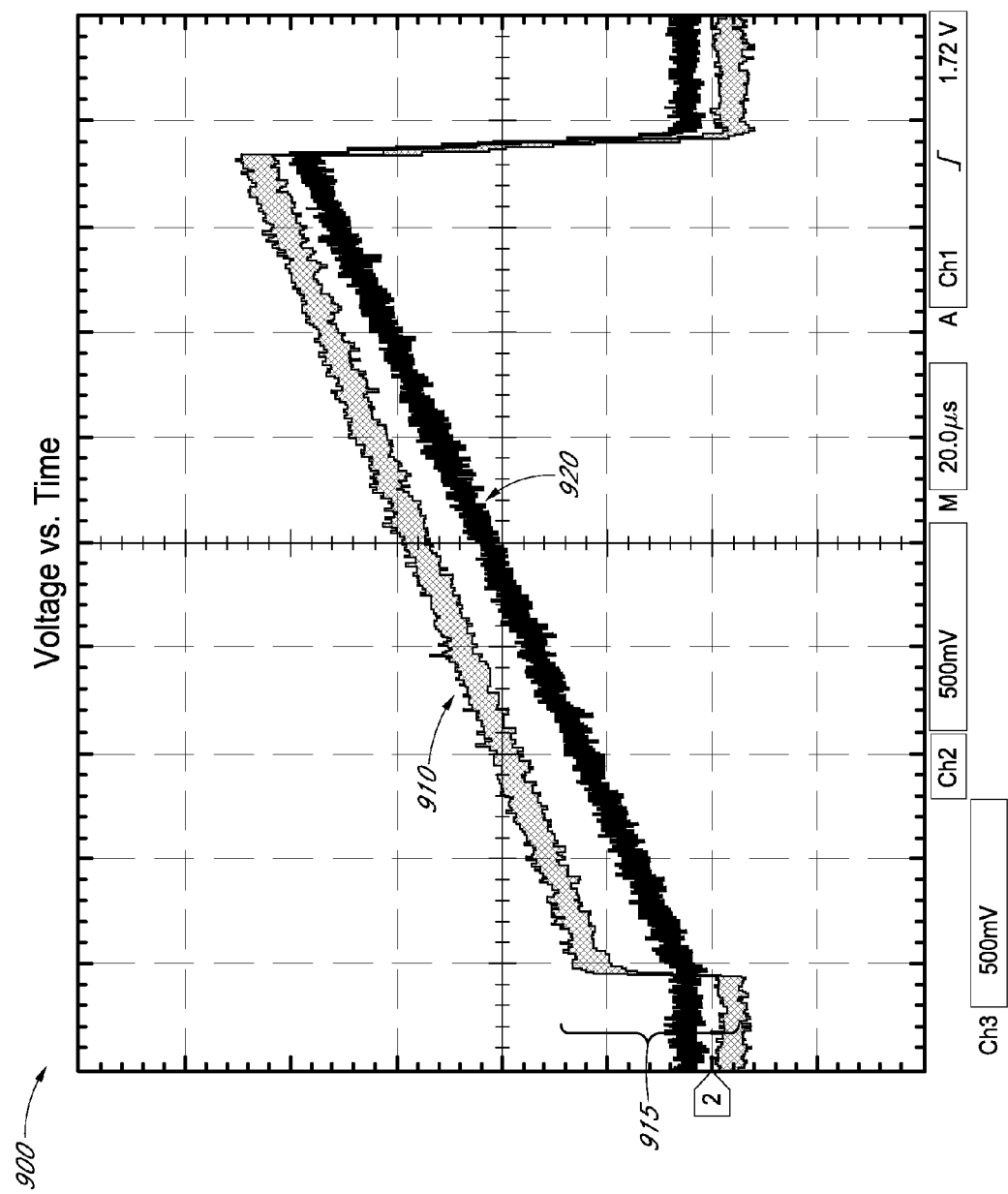
FIG. 9 is a graph of an output voltage signal of an embodiment of an authentication circuit over time.

FIG. 9 is a graph 900 of an output voltage ramp signal 910 of an embodiment of an authentication circuit over time. FIG. 9 also includes a capacitor voltage ramp signal 920. The graph of FIG. 9 may correspond, for example, to an authentication circuit 420 as described above with respect to FIG. 4. As shown in the graph, the output signal 910 experiences a jump 915 in voltage of about 0.3 V at about the time when the capacitor C1 begins to be charged. This jump 915 may result at least in part from a clamping effect of a diode, such as diode D1, which may have a diode drop of about 0.3 V. At the output of the authentication circuit 420, the diode drop can therefore result in the signal effectively being about 0.3 V instead of 0 V in one embodiment. Since this voltage jump can depend at least partly on the diode, if the value of the diode drop is other than 0.3 V, the initial voltage jump value can also be relatively higher. The value of the initial voltage may also be higher due to any voltage remaining on the capacitor from a previous test cycle. Output values provided to a patient monitor by the authentication circuit may be acceptable within a degree of tolerance. Therefore, relatively minor variations in voltage levels may not cause the output signal to fall out of acceptable ranges expected by the patient monitor for purposes of authentication of compatibility or functionality.

FIG. 10 is a graph showing examples of the time it takes an output voltage signal of an embodiment of an authentication circuit to reach a target voltage with respect to a resistance value associated with the authentication circuit. The graph may correspond, for example, to an authentication circuit 420 as described above with respect to FIG. 4. In certain embodiments, a patient monitor may accept, for purposes of authentication, voltage output levels from an authentication circuit that fall within a particular range. Accordingly, values of certain devices of the authentication circuit 420 may be modified and still fall within acceptable ranges, depending on system characteristics. For example, with the value of the capacitor C1 and resistor R3 held constant, FIG. 10 provides the time to reach a target voltage value with respect to different values of R2. The relevant target voltage may be, for example, a value between about 2-5 V (or some other value), plus or minus a range of tolerance. In the depicted embodiment, acceptable times for the output signal to reach the target voltage are shown as being between about 168 μS and about 104 μS. However, these values may differ significantly in some embodiments, depending on the target voltage range or based on other factors.

Figure 11:
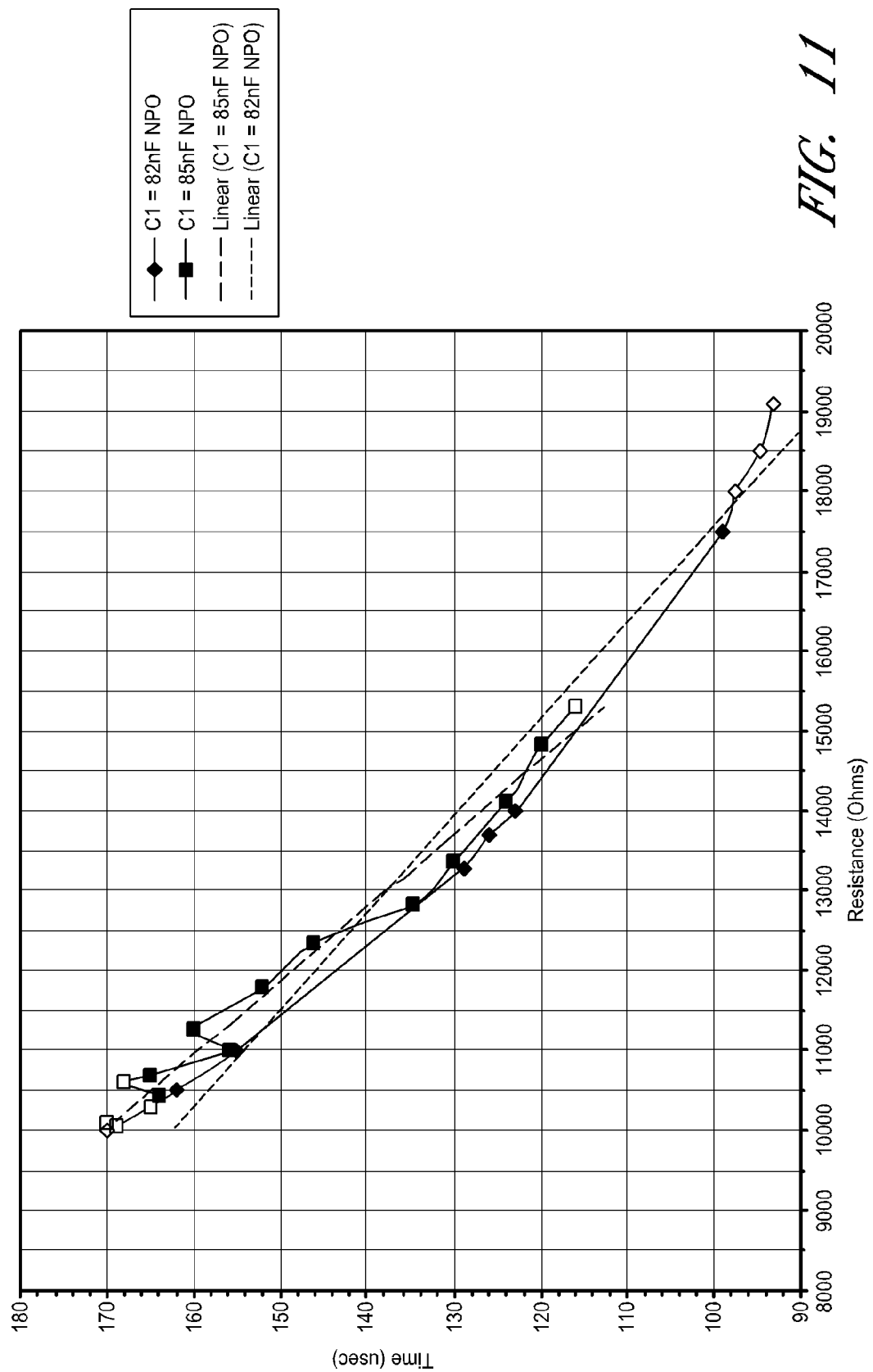
FIG. 11 is a graph showing the time it takes an output voltage signal of an embodiment of an authentication circuit to reach a target voltage with respect to resistance and capacitance values associated with the authentication circuit.

FIG. 11 is a graph showing an example time it may take an output voltage signal of an embodiment of an authentication circuit to reach a target voltage with respect to resistance and capacitance values associated with the authentication circuit. Specifically, with the value of R3 held constant, FIG. 11 shows the time to reach a target voltage value with respect to different values of R2 and C1. It should be noted that the actual time that the linear voltage ramp takes to reach the target voltage can also vary due to component tolerances, component temperature changes, and noise in the authentication circuit, among possibly other factors.

TERMINOLOGY

The headings provided herein, if any, are for convenience only and do not necessarily affect the scope or meaning of the claimed invention. Although the exemplary embodiments are described in relation to a medical cable, embodiments of the present disclosure can be applied in any application where authentication of an electronic device is desired.

Many other variations than those described herein will be apparent from this disclosure. For example, depending on the embodiment, certain acts, events, or functions of any of the algorithms described herein can be performed in a different sequence, can be added, merged, or left out all together (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An exemplary storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A medical cable for transmitting data between a patient monitor and a sensor, the medical cable comprising:
    a cable body;
    a first connector connected to the cable body and configured to be coupled to a patient monitor;
    a second connector connected to the cable body, the second connector configured to be coupled to a sensor and to receive a sensor signal from the sensor that comprises information related to the one or more physiological parameters; and
    an authentication circuit, configured to receive a test signal from the patient monitor and generate an output ramp signal responsive to the test signal that reaches a target voltage within an amount of time expected by the patient monitor, thereby enabling the monitor to authenticate the medical cable,
    wherein the second connector comprises a portion of an electrically conductive path in series with a switch, the conductive path configured to transmit the test signal from the patient monitor to the authentication circuit, said second connector configured to close the switch in response to being coupled to the sensor.

2. The medical cable of claim 1, wherein the authentication circuit is further configured to provide the output ramp signal to the patient monitor.

3. The medical cable of claim 1, wherein the authentication circuit further comprises a diode, wherein the authentication circuit is configured such that activation of the diode allows for the capacitor to at least partially discharge through the diode.

4. The medical cable of claim 1, wherein the test signal is a square wave having a predetermined pulse width.

5. The medical cable of claim 1, wherein the authentication circuit is disposed within the first connector.

6. The medical cable of claim 1, wherein the second connector comprises a housing, the authentication circuit being contained within the housing.

7. The medical cable of claim 1, wherein the second connector comprises a plurality of circuit boards disposed in a parallel configuration, the plurality of circuit boards being perpendicular to a longitudinal axis of the medical cable.

8. The medical cable of claim 1, wherein the transmission of data between the patient monitor and the sensor through the medical cable is partially prohibited when the authentication circuit fails to provide the output signal to the patient monitor at a set time after the sensor and the medical cable are physically connected.

9. The medical cable of claim 1, wherein the target voltage is between about 2 volts to about 4 volts.

10. The medical cable of claim 1, wherein the target time period is between about 100 μS and about 170 μS.

11. A method of transmitting data between a patient monitor and a sensor, the method comprising:
   connecting a medical cable to a patient monitor;
   receiving a test signal with an authentication circuit disposed in the medical cable;
   converting the test signal into a substantially constant current signal;
   generating a ramp signal using the current signal; and
   providing the ramp signal to the patient monitor, thereby enabling the monitor to authenticate the medical cable,
   wherein the transmission of data between the patient monitor and the sensor through the medical cable is partially prohibited when the authentication circuit fails to provide the output signal to the patient monitor at a set time after the sensor and the medical cable are physically connected.

12. The method of claim 11, further comprising:
   receiving a confirmation signal from the patient monitor indicating that the medical cable is in an authenticated state.

13. The method of claim 11, further comprising:
   using the medical cable, transmitting a sensor signal that comprises information related to one or more physiological parameters from a sensor to the patient monitor.

14. A medical cable for transmitting data between a patient monitor and a sensor, the medical cable comprising:
   a cable body;
   a first connector connected to the cable body and configured to be coupled to a patient monitor;
   a second connector connected to the cable body, the second connector configured to be coupled to a sensor and to receive a sensor signal from the sensor; and
   a safety switch configured to be triggered by a connection between the second connector and the sensor, the safety switch configured to be in a first state when the second connector is coupled to the sensor and in a second state when the second connector is not coupled to the sensor.

15. The medical cable of claim 14, wherein the safety switch at least partially prevents the patient monitor from outputting a measurement value when the sensor is not connected to the second connector.

16. The medical cable of claim 14, wherein the first state is an electrically closed state and the second state is an electrically open state.

17. The medical cable of claim 14, wherein the safety switch prevents an authentication circuit disposed in the cable from receiving power from the patient monitor, thereby preventing the authentication circuit from authenticating to the patient monitor.

18. The medical cable of claim 1, wherein the authentication circuit comprises a substantially constant current source coupled to a capacitor configured to generate the output ramp signal.

19. The medical cable of claim 14, wherein the safety switch prevents authentication of the cable to the patient monitor when the safety switch is in the second state.

20. A medical cable for transmitting data between a patient monitor and a sensor, the medical cable comprising:
   a cable body;
   a first connector connected to the cable body and configured to be coupled to a patient monitor;
   a second connector connected to the cable body, the second connector configured to be coupled to a sensor and to receive a sensor signal from the sensor that comprises information related to the one or more physiological parameters; and
   an authentication circuit, configured to receive a test signal from the patient monitor and generate an output ramp signal responsive to the test signal that reaches a target voltage within an amount of time expected by the patient monitor, thereby enabling the monitor to authenticate the medical cable,
   wherein the transmission of data between the patient monitor and the sensor through the medical cable is partially prohibited when the authentication circuit fails to provide the output signal to the patient monitor at a set time after the sensor and the medical cable are physically connected.

21. The medical cable of claim 20, wherein the test signal is a square wave having a predetermined pulse width.

22. The medical cable of claim 20, wherein the authentication circuit is further configured to provide the output ramp signal to the patient monitor.

23. The medical cable of claim 20, wherein the target voltage is between about 2 volts to about 4 volts.

24. The medical cable of claim 20, wherein the target time period is between about 100 μS and about 170 μS.

25. A medical cable for transmitting data between a patient monitor and a sensor, the medical cable comprising:
   a cable body;
   a first connector connected to the cable body and configured to be coupled to a patient monitor;
   a second connector connected to the cable body, the second connector configured to be coupled to a sensor and to receive a sensor signal from the sensor that comprises information related to the one or more physiological parameters; and
   an authentication circuit, configured to receive a test signal from the patient monitor and generate an output ramp signal responsive to the test signal that reaches a target voltage within an amount of time expected by the patient monitor, thereby enabling the monitor to authenticate the medical cable,
   wherein the authentication circuit further comprises a diode and wherein the authentication circuit is configured such that activation of the diode allows for the capacitor to at least partially discharge through the diode.

26. The medical cable of claim 25, wherein the test signal is a square wave having a predetermined pulse width.

27. The medical cable of claim 25, wherein the authentication circuit is further configured to provide the output ramp signal to the patient monitor.

28. The medical cable of claim 25, wherein the target voltage is between about 2 volts to about 4 volts.

29. The medical cable of claim 25, wherein the target time period is between about 100 μS and about 170 μS.

30. A medical cable for transmitting data between a patient monitor and a sensor, the medical cable comprising:
   a cable body;
   a first connector connected to the cable body and configured to be coupled to a patient monitor;
   a second connector connected to the cable body, the second connector configured to be coupled to a sensor and to receive a sensor signal from the sensor that comprises information related to the one or more physiological parameters; and
   an authentication circuit, configured to receive a test signal from the patient monitor and generate an output ramp signal responsive to the test signal that reaches a target voltage within an amount of time expected by the patient monitor, thereby enabling the monitor to authenticate the medical cable,
   wherein the second connector comprises a plurality of circuit boards disposed in a parallel configuration, the plurality of circuit boards being perpendicular to a longitudinal axis of the medical cable.

31. The medical cable of claim 30, wherein the test signal is a square wave having a predetermined pulse width.

32. The medical cable of claim 30, wherein the authentication circuit is further configured to provide the output ramp signal to the patient monitor.

33. The medical cable of claim 30, wherein the target voltage is between about 2 volts to about 4 volts.

34. The medical cable of claim 30, wherein the target time period is between about 100 μS and about 170 μS.

* * * * *